United States Patent [19]

Wey

[11] Patent Number: 5,007,756
[45] Date of Patent: Apr. 16, 1991

[54] BALLPOINT PEN WITH CONDOM

[76] Inventor: Remo C. Wey, 31; Rue pres Guetins, CH-2520 La Neuveville, Switzerland

[21] Appl. No.: 278,947
[22] PCT Filed: Feb. 25, 1988
[86] PCT No.: PCT/CH88/00045
§ 371 Date: Oct. 5, 1988
§ 102(e) Date: Oct. 5, 1988
[87] PCT Pub. No.: WO88/06534
PCT Pub. Date: Sep. 7, 1988

[30] Foreign Application Priority Data

Feb. 25, 1987 [CH] Switzerland ............ 007051/87

[51] Int. Cl.[5] .................................. B43K 29/00
[52] U.S. Cl. ............................ 401/195; 401/52; 401/209
[58] Field of Search ................ 401/16–19, 401/52, 195, 209; 206/38, 69, 216, 537; 220/4 R, 4 A, 4 B, 4 C, 4 D; 221/199, 208, 185, 270; D19/36

[56] References Cited

U.S. PATENT DOCUMENTS

| 470,997 | 3/1892 | Fairchild | 401/52 |
| 2,008,875 | 7/1935 | Peterson et al. | 206/69 |
| 2,354,402 | 7/1944 | Petroccione et al. | 401/18 X |
| 2,594,083 | 4/1952 | Silver | 401/209 X |
| 2,707,552 | 5/1955 | Mattiesen | 206/537 |
| 2,813,289 | 11/1957 | Even | 206/38 R X |
| 3,639,069 | 2/1972 | Gordon | 401/195 |
| 4,174,048 | 11/1979 | Volpe, Jr. | 206/537 X |
| 4,741,434 | 5/1988 | Liebman | 206/69 X |

FOREIGN PATENT DOCUMENTS 927529  4/1955  Fed. Rep. of Germany ........ 206/69

Primary Examiner—Richard J. Apley
Assistant Examiner—D. F. Crosby
Attorney, Agent, or Firm—Lee, Mann, Smith McWilliams & Sweeney

[57] ABSTRACT

A ballpoint pen is provided with a discreetly packed condom and includes a writing head part having a point and filler for writing fluid with a cylindrical shell connected to the writing head part which discreetly contains at least one condom.

1 Claim, 2 Drawing Sheets

FIG. 1
FIG. 2
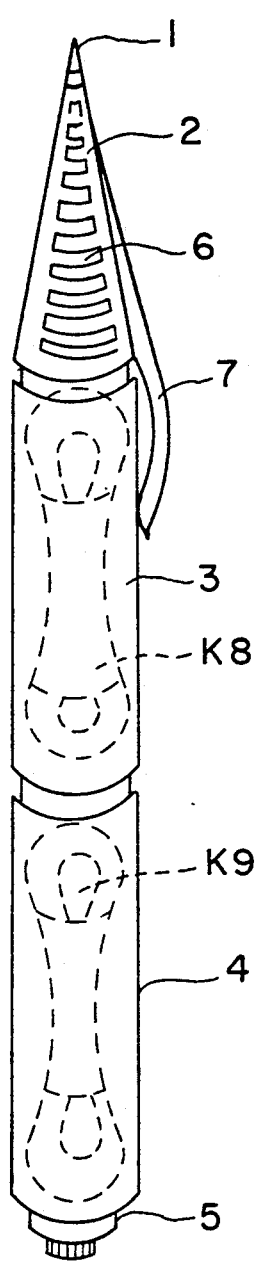
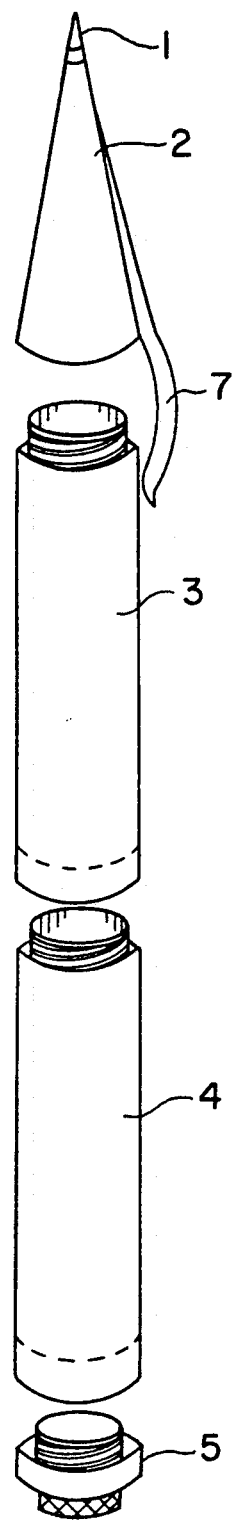

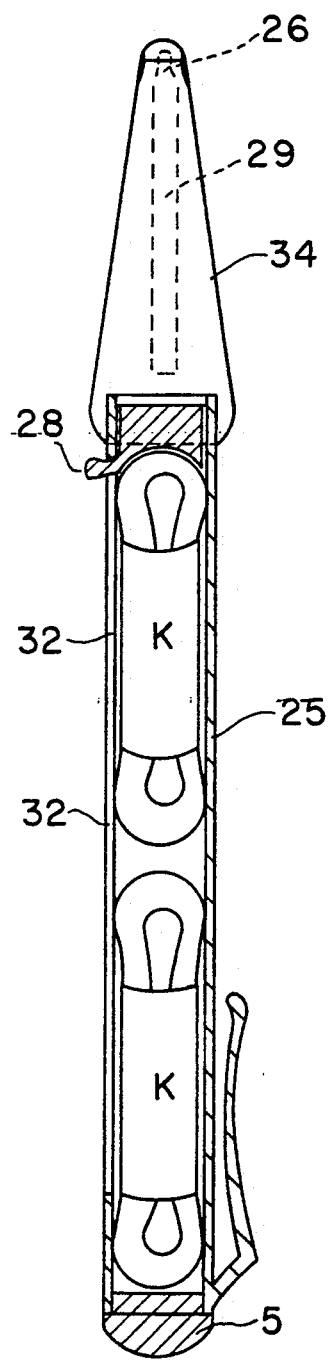

BALLPOINT PEN WITH CONDOM

Applicant claims priority based upon International Application No. PCT/CH88/00045, filed Feb. 25, 1988 and claiming priority of Switzerland patent application No. 007051/88 filed Feb. 25, 1987.

Since the use of condoms has undergone a strong upswing again since the spread of acquired immune deficiency syndrome (AIDS) for the avoidance of infection, there is also the need to carry along the condom well protected from damage and discreetly.

The invention creates for this purpose an ideal possibility of supplying condoms in a ballpoint pen; its essential features are yielded from the patent claim.

Embodiments of the invention are explained in detail with the aid of the drawing, in which:

FIGS. 1 and 2 show a ballpoint pen with separatable shell; and,

FIG. 3 shows an embodiment with a special device for pushing the condoms out of the shell.

The ballpoint pen represented in FIG. 1 has a writing head with a writing point 1, a conical shell 2 provided with a clip 7, into which there is installed the conical writing-fluid container or filler 6. To the head there is attached a first partial shell 3 containing a condom K-8, preferably screwed on and to this again in like manner another shell 4 with a condom K-9. This second partial shell 4 is closed by a screwed-on or slipped-on cap 5. Through the decomposable construction of the shell the condoms can conveniently be removed singly. The partial shells can, for example, be provided on face side with an outside thread and on rear side with an inside thread, without other possibilities of connection being excluded here. The construction makes it possible, therefore, to place the condoms K8, K9 in such partial shells on the market as disposable packing. In the embodiment according to FIG. 3 the writing point is designated with 26 and the filler with 29. The writing head is firmly joined with the shell 25 in which there are accommodated two condoms K. The shell 25 has a longitudinal slit 32, in which there is guided a pushing head of a push plate 28. It is easily evident that by this pushing member 28 the condoms can conveniently be pushed out of the shell 25. The cover shell for the writing head is here designed with 34.

I claim:

1. A ballpoint pen with a discreetly packed condom comprising a non-retractable writing head part connected to a cylindrical shell, the writing head part having a writing point connected to a filler containing writing fluid, wherein the cylindrical shell consists of individual cylindrical shells each being open at both ends, each of said cylindrical shells accommodating one condom, said cylindrical shells being threadably connectable with one another and threadably connectable with said writing head part, and the cylindrical shells having means for removing a condom.

* * * * *